United States Patent [19]

Konz et al.

[11] 3,998,953
[45] Dec. 21, 1976

[54] 1,3,7-TRISUBSTITUED XANTHINE PERIPHERAL VASODILATORS

[75] Inventors: Wilhelm Konz; Richard Reichl, both of Ingelheim am Rhein, Germany

[73] Assignee: Boehringer Ingelheim GmbH, Ingelheim am Rhein, Germany

[22] Filed: Dec. 17, 1975

[21] Appl. No.: 641,550

[30] Foreign Application Priority Data

Dec. 21, 1974  Germany .................. 2460929

[52] U.S. Cl. .................. 424/253; 260/256
[51] Int. Cl.[2] .................. A61K 31/52; C07D 57/48
[58] Field of Search .................. 260/256; 424/253

[56] References Cited

UNITED STATES PATENTS

| | | | |
|---|---|---|---|
| 3,565,896 | 2/1971 | Ghielmetti et al. | 260/256 |
| 3,728,346 | 4/1973 | Klingler | 260/256 |
| 3,896,127 | 7/1975 | Takahashi et al. | 260/256 |

*Primary Examiner*—Leonard Schenkman
*Attorney, Agent, or Firm*—Hammond & Littell

[57] ABSTRACT

Compounds of the formula

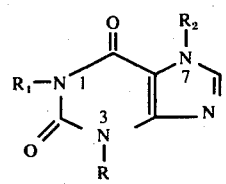

wherein
R is methyl or ethyl,
R₁ is methyl, ethyl or

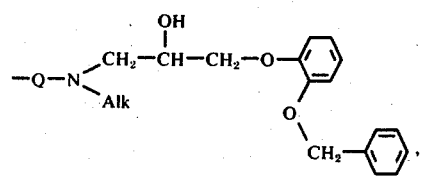

and
R₂ is methyl, ethyl,

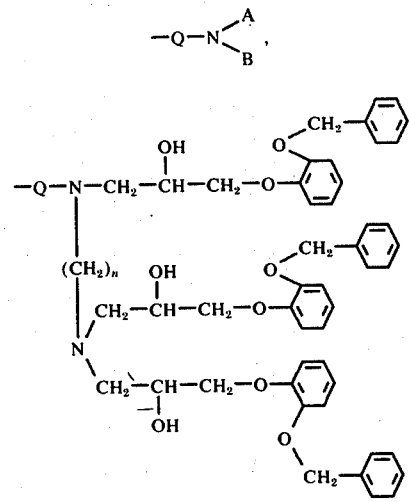

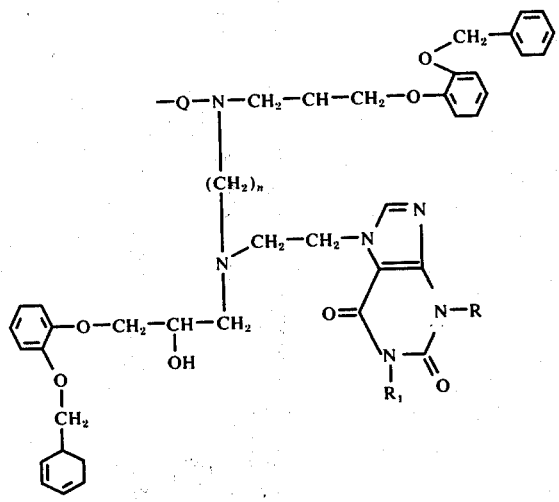

where
Alk is alkyl of 1 to 4 carbon atoms,
Q is ethyl, propyl, isopropyl or 2-hydroxy-propyl,
A is 3-phenoxy-2-hydroxy-propyl, where the phenyl ring is substituted in the o-position by hydroxy, methoxy, n-hexyloxy or benzyloxy,
B is alkyl of 1 to 4 carbon atoms, phenyl, p-methylphenyl, 3-phenyl-3-hydroxy-isopropyl or A, as defined above, and
n is an integer from 2 to 6, inclusive, provided, however, that one of R₁ and R₂ must be methyl or ethyl and the other has one of the other respective meanings indicated; and non-toxic, pharmacologically acceptable acid addition salts thereof. The compounds as well as the salts are useful as peripheral vasodilators.

4 Claims, No Drawings

1,3,7-TRISUBSTITUED XANTHINE PERIPHERAL VASODILATORS

This invention relates to novel 1,3,7-trisubstituted xanthines and non-toxic acid addition salts thereof, as well as to methods of preparing these compounds.

More particularly, the present invention relates to a novel class of 1,3,7-trisubstituted xanthines represented by the formula

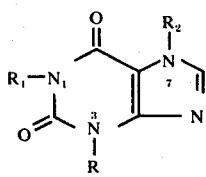
(I)

wherein
R is methyl or ethyl,
$R_1$ is methyl, ethyl or

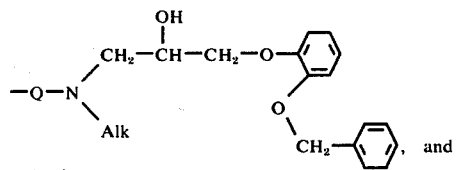, and and
$R_2$ is methyl, ethyl,

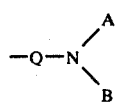

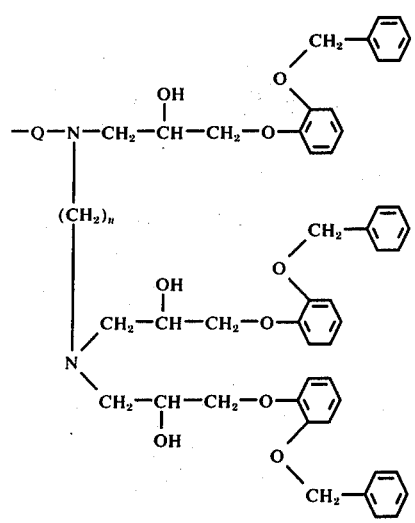

or

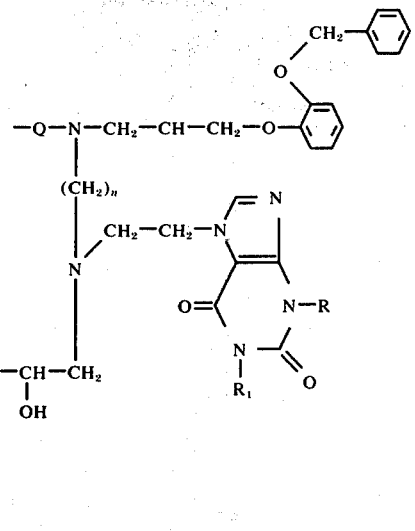

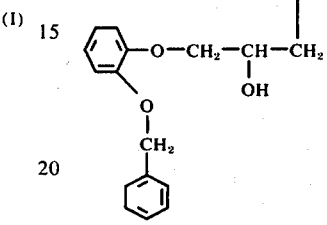

where
Alk is alkyl of 1 to 4 carbon atoms,
Q is ethyl, propyl, isopropyl, or 2-hydroxy-propyl,
A is 3-phenoxy-2-hydroxy-propyl, where the phenyl ring is substituted in the o-position by hydroxy, methoxy, n-hexyloxy or benzyloxy,
B is alkyl of 1 to 4 carbon atoms, phenyl, p-methyl-phenyl, 3-phenyl-3-hydroxy-isopropyl or A, as defined above, and
n is an integer from 2 to 6, inclusive, provided, however, that one of $R_1$ and $R_2$ must be methyl or ethyl and the other has one of the other respective meanings defined above; and non-toxic, pharmacologically acceptable acid addition salts thereof.

The compounds embraced by formula I may be prepared by the following methods:

METHOD A

1. By reacting a 1-(2,3-epoxy-propyl)-substituted xanthine of the formula

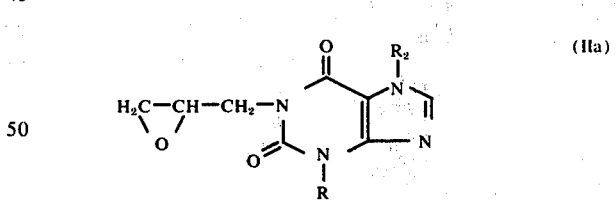
(IIa)

wherein R and $R_2$ are each methyl or ethyl, with a secondary amine of the formula

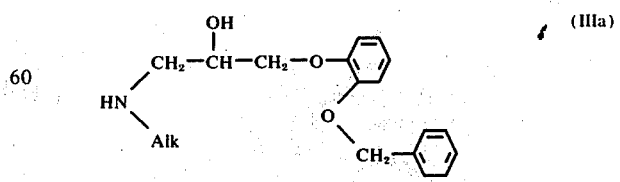
(IIIa)

wherein Alk is alkyl of 1 to 4 carbon atoms; or 2. by reacting a 7-(2,3-epoxy-propyl)-substituted xanthine of the formula

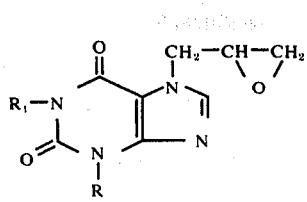 (IIb)

wherein R and R₁ are each methyl or ethyl, with a secondary amine of the formula

 (IIIb)

wherein A and B have the same meanings as in formula I.

METHOD B

For the preparation of a compound of the formula I wherein Q is ethyl, propyl or isopropyl, 1. by reacting a 7-(amino-alkyl)-substituted xanthine of the formula

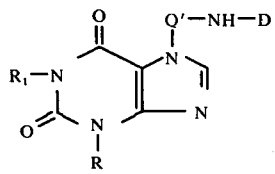 (IV)

wherein

R₁ and R are each methyl or ethyl,
Q' is ethyl, propyl or isopropyl, and
D is hydrogen, alkyl of 1 to 4 carbon atoms, phenyl, p-tolyl, amino-(alkyl of 2 to 6 carbon atoms) or N-[β-(1,3-dimethyl-xanthin-7-yl)-ethyl]-amino(alkyl of 3 to 6 carbon atoms),
with a 1-phenoxy-2,3- epoxy-propane of the formula

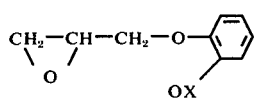 (V)

wherein X is benzyl or n-hexyl; or 2. by reacting a haloalkyl-substituted xanthine of the formula

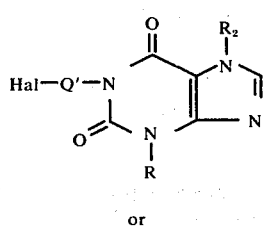 (VIa)

or

-continued

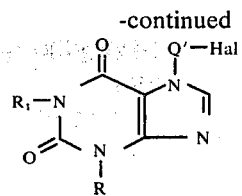 (VIb)

wherein
R, R₁ and Q' have the meanings previously defined, and
Hal is halogen,
with a secondary amine of the formula $$HN-CH_2-CH-CH_2-O-\phenyl \quad (VII)$$
$$\ \ \ |\ \ \ \ \ \ \ \ \ \ |$$
$$\ \ \ Y\ \ \ \ \ \ \ OH\ \ \ \ \ \ OX$$

wherein
Y is alkyl of 1 to 4 carbon atoms, and
X has the same meanings as in formula V.

The reactions pursuant to methods A and B(1) are carried out by heating a mixture of the reactants, optionally in the presence of an inert solvent, such as benzene, toluene, xylene, mesitylene or dioxane; without a solvent the operative reaction temperature range is about 160°–220° C, but if a solvent is used the reaction is carried out at the reflux temperature. The reaction time varies between about 15 minutes and several hours, depending upon the reactivity of the reactants. If no solvent is used, the reaction mixture is then allowed to cool to about 60°–80° C, admixed with a suitable solvent, preferably a lower alkanol, and the resulting solution containing the free base form of the desired reaction product is adjusted to pH 1 by addition of an inorganic or organic acid to form the desired acid addition salt. The salt is recovered from the acidic reaction mixture in conventional manner.

Examples of non-toxic, pharmacologically acceptable acid addition salts are those formed with a hydrohalic acid, nitric acid, sulfuric acid, phosphoric acid, oxalic acid, citric acid, tartaric acid, maleic acid, propionic acid, butyric acid, acetic acid, methansulfonic acid, toluenesulfonic acid, succinic acid, nicotinic acid, cyclohexylaminesulfonic acid, 8-chlorotheophylline or the like.

The reaction pursuant to method B(2) is effected by dissolving the reaction components in a suitable solvent, such as dioxane water, dimethylformamide/water or an alcohol, and refluxing the solution until the reaction is finished. Here, too, the reaction mixture is further worked up in the usual way.

Some of the starting compounds of the formulas IIa, IIb and IV are also new, but they may all be prepared by known methods.

For instance, a compound of the formula IIa may be prepared by reacting the sodium salt of a 3,7-dialkyl-xanthine with an excess of epichlorohydrin; a compound of the formula IIb may be obtained in analogous fashion from the sodium salt of a 1,3-dialkyl-xanthine.

A compound of the formula IV may be obtained by reacting a 1,3-dialkyl-xanthine with a corresponding chloroalkanol, replacing the hydroxyl group by a chlorine atom by means of thionyl chloride, and reacting the resulting 7-chloroalkyl-1,3-dialkyl-xanthine with a correspondingly substituted amine.

The following examples illustrate the present invention and will enable others skilled in the art to understand it more completely. It should be understood, however, that the invention is not limited solely to the particular examples given below.

EXAMPLE 1

7-{2-[N-[3-(o-Benzyloxy-phenoxy)-2-hydroxy-1-propyl]-N-methyl-amino]-ethyl}-1,3-diethyl-xanthine and its hydrochloride by method B(1)

113 gm of 1,3-diethyl-7-(β-methylamino-ethyl)-xanthine (m.p. 101°–104° C) were thoroughly admixed with 114.8 gm of 1-epoxy-propyl 2-benzyloxyphenyl ether, and the mixture was heated for 30 minutes at a temperature between 180°–190° C. Thereafter, the resulting clear, yellowish-brown molten mass was allowed to cool to 80° C and was then dissolved in ethanol. The ethanolic solution, which contained the free base reaction product, was acidified with ethanolic hydrochloric acid to pH 1, cooled to room temperature, and admixed with a little absolute ether. The crystals which had separated out after three hours of standing at room temperature were collected by suction filtration and then washed with a mixture of ethanol and ether (3:1), yielding 190.6 gm (77% of theory) of the hydrochloride of the formula

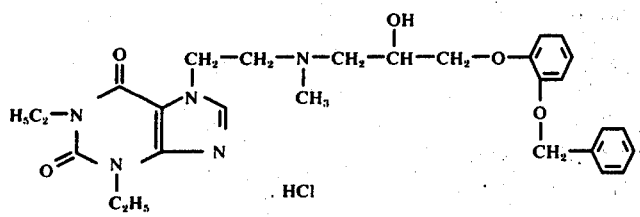

which had a melting point of 85°–90° C.

EXAMPLE 2

7-{3-[N-[3-(o-Benzyloxy-phenoxy)-2-hydroxy-1-propyl]-N-n-butyl-amino]-2-hydroxy-1-propyl}-1,3-diethyl-xanthine and its hydrochloride by method A(2)

5.28 gm of 1,3-diethyl-7-(2,3-epoxypropyl)-xanthine were thoroughly admixed with 6.58 gm of N-[3-(o-benzyloxyphenoxy)-2-hydroxy-1-propyl]-N-n-butyl-amine, and the mixture was heated at about 170° C for 15 minutes. Thereafter, the resulting molten mass was cooled to 80° C and then dissolved by refluxing with 50 ml of absolute ethanol. The resulting solution, which contained the free base reaction product, was cooled to room temperature and then acidified with ethanolic hydrochloric acid to pH 1. The crystals formed thereby were collected by suction filtration and washed with a mixture of ethanol and ether (1:3), yielding 12.5 gm (96% of theory) of the hydrochloride of the formula

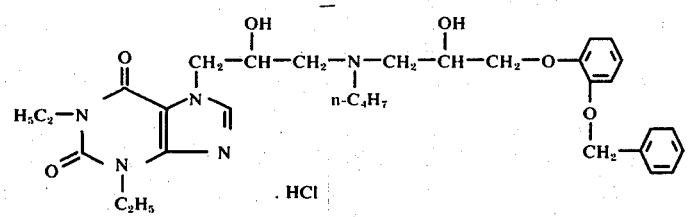

which had a melting point of 144°–149° C.

In analogous manner, using analogous starting compounds, the following additional compounds of the formula I and non-toxic acid addition salts thereof were prepared:

a. 7-{2-[N,N-bis-[3-(o-benzyloxy-phenoxy)-2-hydroxy-1-propyl]-amino]-ethyl}-1,3-dimethyl-xanthine, m.p. 132°–138° C, of the formula

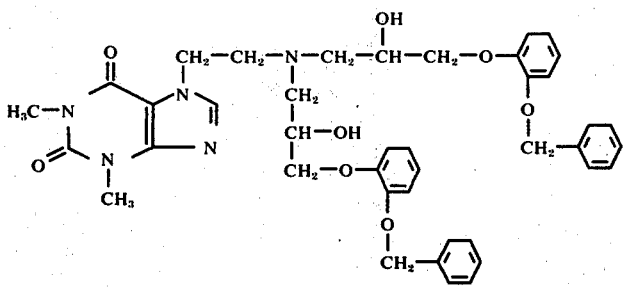

b. 7-{3-[N-[3-(o-methoxy-phenoxy)-2-hydroxy-1-propyl]-N-(2-phenyl-2-hydroxy-isopropyl)-amino]-2-hydroxy-1-propyl}-1,3-dimethyl-xanthine dihydrochloride, m.p. 181°–183° C.

c. 7-{2-[N-[3-(o-benzyloxy-phenoxy)-2-hydroxy-1-propyl]-N-phenyl-amino]-ethyl}-1,3-dimethylxanthine hydrochloride, m.p. 102° C.

d. 7-{2-[N-[3-(o-benzyloxy-phenoxy)-2-hydroxy-1-propyl]-N-(p-tolyl)-amino]-ethyl}-1,3-dimethyl-xanthine hydrochloride, m.p. 176°–179° C.

e. 7-{2-[N-[3-(o-benzyloxy-phenoxy)-2-hydroxy-1-propyl]-N-n-butyl-amino]-ethyl}-1,3-dimethyl-xanthine hydrochloride, m.p. 176°–180° C.

f. 7-{2-[N-[3-(o-benzyloxy-phenoxy)-2-hydroxy-1-propyl]-N-ethyl-amino]-ethyl}-1,3-dimethyl-xanthine hydrochloride, m.p. 166°–169° C.

g. 7-{2-[N,N-bis-[3-(o-benzyloxy-phenoxy)-2-hydroxy-1-propyl]-amino]-ethyl}-1,3-diethyl-xanthine hydrochloride, m.p. 60° C.

h. 7-{2-[N-[3-(o-benzyloxy-phenoxy)-2-hydroxy-1-propyl]-N-ethyl-amino]-ethyl}-1,3-diethyl-xanthine hydrochloride, m.p. 115°–116° C.

i. 7-{2-[N-[3-(o-hydroxy-phenoxy)-2-hydroxy-1-propyl]-N-ethyl-amino]-ethyl}-1,3-diethyl-xanthine hydrochloride, m.p. 172°–176° C.

j. 7-{3-[N-[3-(o-benzyloxy-phenoxy)-2-hydroxy-1-propyl]-N-ethyl-amino]-2-hydroxy-1-propyl}-1,3-dimethyl-xanthine hydrochloride, m.p. 148°–150° C.

k. 7-{3-[N-[3-(o-benzyloxy-phenoxy)-2-hydroxy-1-propyl]-N-methyl-amino]-2-hydroxy-1-propyl}-1,3-diethyl-xanthine hydrochloride, m.p. 114°–116° C.

l. 7-{3-[N-[3-(o-benzyloxy-phenoxy)-2-hydroxy-1-propyl]-N-methyl-amino]-2-hydroxy-1-propyl}-1,3-dimethyl-xanthine hydrochloride, m.p. 172°–175° C.

m. 1-{3-[N-[3-(o-benzyloxy-phenoxy)-2-hydroxy-1-propyl]-N-methyl-amino]-2-hydroxy-1-propyl}-3,7-dimethyl-xanthine tartrate, m.p. 90° C (decomp.), of the formula o. 1-{3-[N-[3-(o-benzyloxy-phenoxy)-2-hydroxy-1-propyl]-N-methyl-amino]-2-hydroxy-1-propyl}-3,7-diethyl-xanthine tartrate, m.p. 59°–64° C.

p. 1-{3-[N-[3-(o-benzyloxy-phenoxy)-2-hydroxy-1-propyl]-N-n-butyl-amino]-2-hydroxy-1-propyl}-3,7-diethyl-xanthine tartrate, m.p. 67°–70° C.

q. 1-{3-[N-[3-)o-benzyloxy-phenoxy)-2-hydroxy-1-propyl]-N-methyl-amino]-1-propyl}-3,7-dimethyl-xanthine hydrochloride, m.p. 169°–170° C.

r. 7-{2-[N-[3-o-n-hexyloxy-phenoxy)-2-hydroxy-1-propyl]-N-ethyl-amino]-ethyl}-1,3-diethyl-xanthine dihydrochloride, m.p. 149°–151° C.

s. 7-{2-[N-[3-(o-n-hexyloxy-phenoxy)-2-hydroxy-1-propyl]-N-methyl-amino]-ethyl}-1,3-diethyl-xanthine oxalate, m.p. 118°–122° C.

t. 7-{3-[N-[3-(o-benzyloxy-phenoxy)-2-hydroxy-1-propyl]-N-n-butyl-amino]-1-propyl}-1,3-dimethyl-xanthine tartrate, m.p. 91° C (decomp.).

u. 7-{3-[N-[3-(o-benzyloxy-phenoxy)-2-hydroxy-1-propyl]-N-methyl-amino]-1-propyl}-1,3-dimethyl-xanthine hydrochloride, m.p. 150°–153° C.

v. 7-{2-[N-[3-(o-benzyloxy-phenoxy)-2-hydroxy-1-propyl]-N-methyl-amino]-ethyl}-1,3-dimethyl-xanthine hydrochloride, m.p. 156°–158° C.

w. 7-{2-[N-[3-(o-benzyloxy-phenoxy)-2-hydroxy-1-propyl]-N-[2-[N',N'-bis-[3-(o-benzyloxy-phenoxy)-2-hydroxy-1-propyl]-amino]-ethyl]-amino]-ethyl}-1,3-dimethyl-xanthine dihydrochloride, m.p. 75°–79° C, of the formula

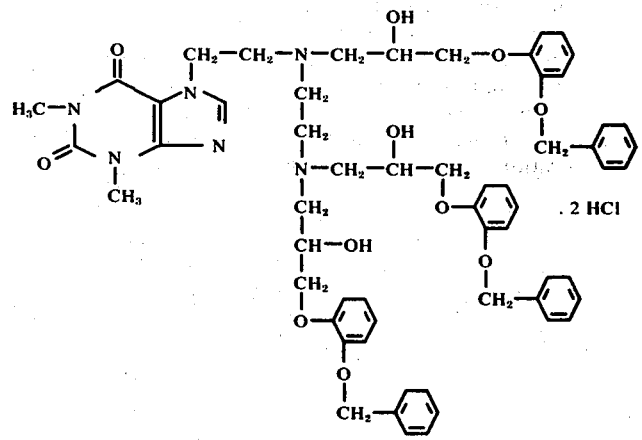

x. 7-{2-[N-[3-(o-benzyloxy-phenoxy)-2-hydroxy-1-propyl]-N-[3-[N',N'-bis-[3-(o-benzyloxy-phenoxy)-2-

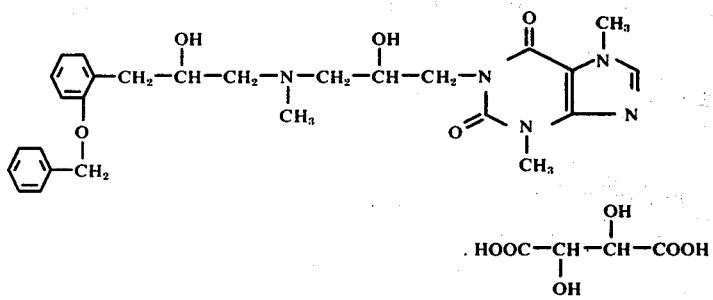

n. 1-{3-[N-[3-(o-benzyloxy-phenoxy)-2-hydroxy-1-propyl]-N-n-butyl-amino]-2-hydroxy-1-propyl}-3,7-dimethyl-xanthine tartrate, m.p. 67°–68° C.

hydroxy-1-propyl]-amino]-1-propyl]-amino]-ethyl}-1,3-dimethyl-xanthine dihydrochloride, m.p. 105°–110° C.

y. 7-{2-[N-[3-(o-benzyloxy-phenoxy)-2-hydroxy-1-propyl]-N-[6-[N',N'-bis-[3-(o-benzyloxy-phenoxy)-2-hydroxy-1-propyl]-amino]-6-n-hexyl]-isopropyl}-1,3-dimethyl-xanthine dihydrochloride; m.p. 60°-65° C.

z. 1,6-bis-{N,N'-(1,3-dimethyl-xanthin-7-yl-ethyl)-N,N'-[3-(o-benzyloxy-phenoxy)-2-hydroxy-1-propyl]}-hexamethylenediamine trihydrobromide, m.p. 125°-130° C, of the formula

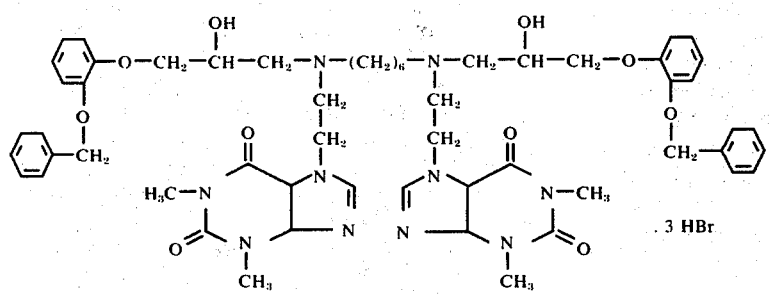

. 3 HBr aa. 1,3-bis-{N,N'-(1,3-dimethyl-xanthin-7-yl-ethyl)-N,N'-[3-(o-benzyloxy-phenoxy)-2-hydroxy-1-propyl]}-propylenediamine dihydrochloride, m.p. 127°-130° C.

The compounds of the present invention, that is, those embraced by formula I above and their non-toxic, pharmacologically acceptable acid addition salts, have useful pharmacodynamic properties. More particularly, they exhibit peripheral vasodilating activities in warm-blooded animals, such as rats, cats and dogs, and are therefore useful for enhancing the peripheral blood flow in the microcirculatory area, especially in the peripheral vessels of the brain. In this respect the compounds of this invention are significantly superior to the related known peripheral vasodilator xanthinol nicotinate disclosed in German Pat. No. 1,102,750, with respect to effectiveness and duration of effective action.

For pharmaceutical purposes the compounds according to the present invention are administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. The effective dosage unit range of the compounds according to the present invention is from 0.08 to 8.33 mgm kg body weight, depending upon the route of administration. For instance, the effective oral dosage unit range is 0.16 to 8.33 mgm kg, preferably 0.83 to 3.33 mgm/kg, with a daily dose rate of 0.5 to 25 mgm/kg, preferably 2.5 to 10 mgm/kg. The effective dosage unit range for parenteral administration, especially by injection, is 0.08 to 3.33 mgm/kg, preferably 0.16 to 1.67 mgm kg.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 3

| | |
|---|---|
| 7-{ 2-[N-[3-(o-Benzyloxy-phenoxy)-2-hydroxy-1-propyl]-N-methyl-amino]-ethyl }-1,3-diethyl-xanthine hydrochloride | 250.0 parts |
| Corn starch | 450.0 parts |
| Lactose | 230.0 parts |
| Soluble starch | 60.0 parts |
| Magnesium stearate | 10.0 parts |
| Total | 1000.0 parts |

Preparation

The xanthine derivative, the lactose and the corn starch are intimately admixed with each other, the mixture is granulated in conventional fashion with an aqueous solution of the soluble starch, the granulate is dried and then intimately admixed with the magnesium stearate, and the resulting composition is compressed into 100 mgm-tablets in a conventional tablet making machine. Each tablet contains 250 mgm of the xanthine derivative and is an oral dosage unit composition with effective peripheral vasodilating action.

EXAMPLE 4

| | |
|---|---|
| 7-{ 3-[N-[3-(o-Benzyloxy-phenoxy)-2-hydroxy-1-propyl]-N-n-butyl-amino]-2-hydroxy-1-propyl }-1,3-diethyl-xanthine dihydrochloride | 300.0 parts |
| Corn starch | 400.0 parts |
| Lactose | 250.0 parts |
| Magnesium stearate | 20.0 parts |
| Gelatin | 30.0 parts |
| Total | 1000.0 parts |

Preparation

The xanthine derivative, the lactose and the corn starch are intimately admixed with each other, the mixture is granulted through a 1 mm-mesh screen with the aid of an aqueous 10% solution of the gelatin, and the granulate is dried at 40° C and again passed through the screen. The resulting dry granulate is admixed with the magnesium stearate, the composition is compressed into 1000 mgm-pill cores which are subsequently coated with a thin shell consisting of a mixture of sugar, titanium dioxide, talcum and gum arabic, and finally polished with beeswax. Each coated pill contains 300 mgm of the xanthine derivative and is an oral dosage unit composition with effective peripheral vasodilating action.

EXAMPLE 5

Hypodermic solution

The solution is conpounded from the following ingredients:

| | | |
|---|---|---|
| 7- { 2-[N-[3-(o-Benzyloxy-phenoxy)-2-hydroxy-1-propyl]-N-methyl-amino]-ethyl } -1,3-diethyl-xanthine hydrochloride | | 40.0 parts |
| Sodium chloride | | 18.0 parts |
| Distilled water | q.s.ad | 2000.0 parts by vol. |

Preparation

The xanthine derivative and the sodium chloride are dissolved in a sufficient amount of distilled water, the solution is diluted to the indicated volume with distilled water, the finished solution is filtered until sterile, and the filtrate is filled into 5 ml-ampules under aseptic conditions; the filled ampules are finally sterilized and sealed. The contents of each ampule are an injectable dosage unit composition with effective peripheral vasodilating action.

Analogous results are obtained when any one of the other xanthine derivatives embraced by formula I or a nontoxic, pharmacologically acceptable acid addition salt thereof is substituted for the particular xanthine compound in Examples 3 through 5. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:
1. A compound of the formula

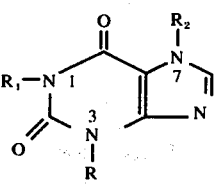

wherein
R is methyl or ethyl,
$R_1$ is methyl, ethyl or

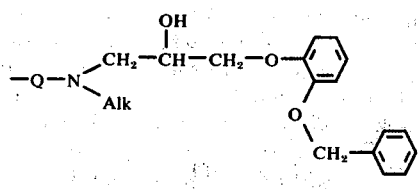

$R_2$ is methyl, ethyl,

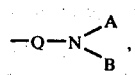

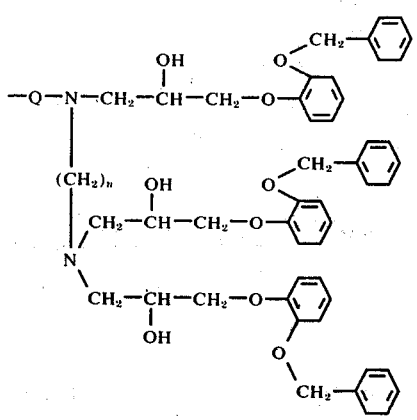

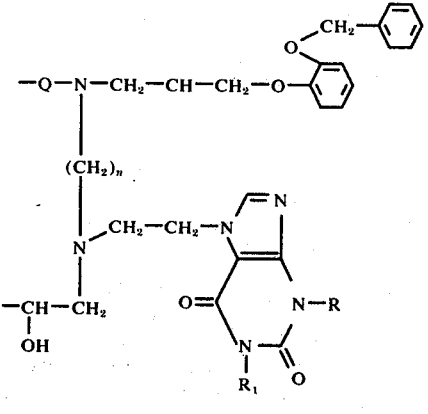

where
Alk is alkyl of 1 to 4 carbon atoms,
Q is ethyl, propyl, isopropyl or 2-hydroxy-propyl,
A is 3-phenoxy-2-hydroxy-propyl, where the phenyl ring is substituted in the o-position by hydroxy, methoxy, n-hexyloxy or benzyloxy,
B is alkyl of 1 to 4 carbon atoms, phenyl, p-methyl-phenyl, 3-phenyl-3-hydroxy-isopropyl or A, as defined above, and
n is an integer from 2 to 6, inclusive,
provided, however, that one of $R_1$ and $R_2$ must be methyl or ethyl and the other has one of the other indicated meanings; or a non-toxic, pharmacologically acceptable acid addition salt thereof.

2. A compound of claim 1, which is 7-{2-[N-[3-o-benzyloxy-phenoxy)-2-hydroxy-1-propyl]-N-methyl-amino]-ethyl}-1,3-diethyl-xanthine or a non-toxic, pharmacologically acceptable acid addition salt thereof.

3. A pharmaceutical dosage unit composition consisting essentially of an inert pharmaceutical carrier and an effective peripheral vasodilating amount of a compound of claim 1.

4. The method of dilating the peripheral blood vessels of a warm-blooded animal in need of such treatment, which comprises perorally or parenterally administering to said animal an effective peripheral vasodilating amount of a compound of claim 1.

* * * * *

UNITED STATES PATENT OFFICE
CERTIFICATE OF CORRECTION

Patent No. 3,998,953     Dated December 21, 1976

Inventor(s) WILHELM KONZ and RICHARD REICHL

It is certified that error appears in the above-identified patent and that said Letters Patent are hereby corrected as shown below:

| | |
|---|---|
| Col. 9, line 3 | After "-hexyl]-" insert -- amino] -- |
| Col. 10, after line 1 | Insert -- Tablets<br><br>The tablet composition is compounded from the following ingredients: -- |
| Col. 10, after line 37 | Insert -- Coated Pills<br><br>The pill core composition is compounded from the following ingredients: -- |

Signed and Sealed this

First Day of March 1977

[SEAL]

Attest:

RUTH C. MASON
Attesting Officer

C. MARSHALL DANN
Commissioner of Patents and Trademarks